(12) United States Patent
Smith et al.

(10) Patent No.: US 8,433,411 B2
(45) Date of Patent: *Apr. 30, 2013

(54) HEADER DESIGN FOR IMPLANTABLE PULSE GENERATOR

(75) Inventors: Galen L. Smith, Allen, TX (US); Timothy J. Cox, Leonard, TX (US)

(73) Assignee: Advanced Neuromodulation Systems, Inc., Plano, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 13/479,058

(22) Filed: May 23, 2012

(65) Prior Publication Data

US 2012/0232617 A1    Sep. 13, 2012

Related U.S. Application Data

(63) Continuation of application No. 12/100,814, filed on Apr. 10, 2008, now Pat. No. 8,190,259.

(60) Provisional application No. 60/910,941, filed on Apr. 10, 2007.

(51) Int. Cl.
  *A61N 1/372* (2006.01)
(52) U.S. Cl.
  USPC .............................................. 607/37; 607/36
(58) Field of Classification Search .................... 607/37, 607/36
  See application file for complete search history.

(56) References Cited

U.S. PATENT DOCUMENTS

| | | | |
|---|---|---|---|
| 6,112,121 A * | 8/2000 | Paul et al. ..................... | 607/37 |
| 6,198,969 B1 | 3/2001 | Kuzma | |
| 6,741,892 B1 | 5/2004 | Meadows et al. | |
| 6,895,276 B2 | 5/2005 | Kast et al. | |
| 7,083,474 B1 | 8/2006 | Frleck et al. | |
| 7,244,150 B1 | 7/2007 | Brase et al. | |
| 7,590,451 B2 | 9/2009 | Tronnes et al. | |
| 7,630,768 B1 * | 12/2009 | Coffed et al. .................. | 607/37 |
| 7,798,864 B2 | 9/2010 | Barker et al. | |
| 8,190,259 B1 * | 5/2012 | Smith et al. ................... | 607/37 |
| 2005/0027326 A1 | 2/2005 | Ries et al. | |
| 2005/0203584 A1 * | 9/2005 | Twetan et al. ................. | 607/36 |
| 2005/0245982 A1 | 11/2005 | Kast et al. | |
| 2006/0030204 A1 * | 2/2006 | Jones et al. ................... | 439/488 |
| 2009/0247018 A1 | 10/2009 | Kast et al. | |

* cited by examiner

*Primary Examiner* — Eric D. Bertram

(57) ABSTRACT

In one embodiment, an implantable pulse generator for electrically stimulating a patient comprises: a metallic housing enclosing pulse generating circuitry; a header mechanically coupled to the metallic housing, the header adapted to seal terminals of one or more stimulation leads within the header and to provide electrical connections for the terminals; the header comprising an inner compliant component for holding a plurality of electrical connectors, the plurality of electrical connectors electrically coupled to the pulse generating circuitry through feedthrough wires, wherein the plurality of electrical connectors are held in place in recesses within the compliant inner component, the header further comprising an outer shield component adapted to resist punctures, the outer shield component fitting over at least a portion of the inner compliant component.

12 Claims, 4 Drawing Sheets

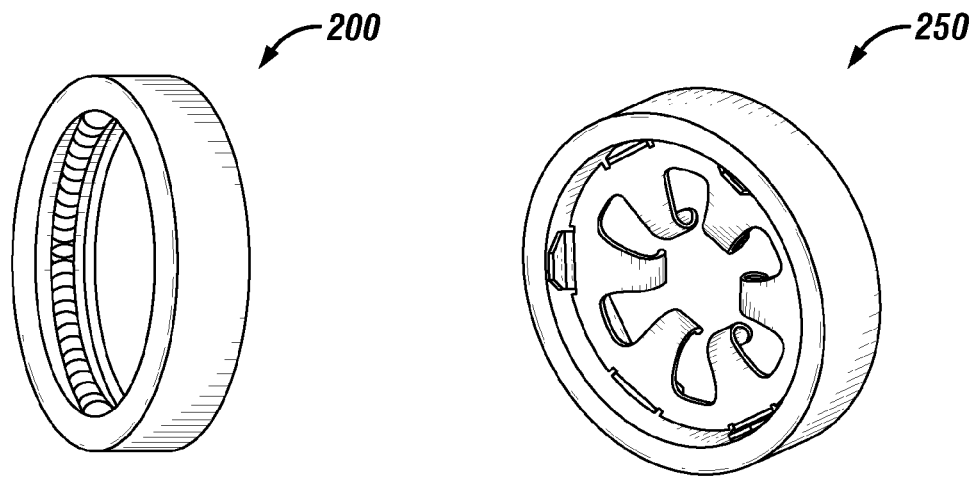
FIG. 2A  FIG. 2B
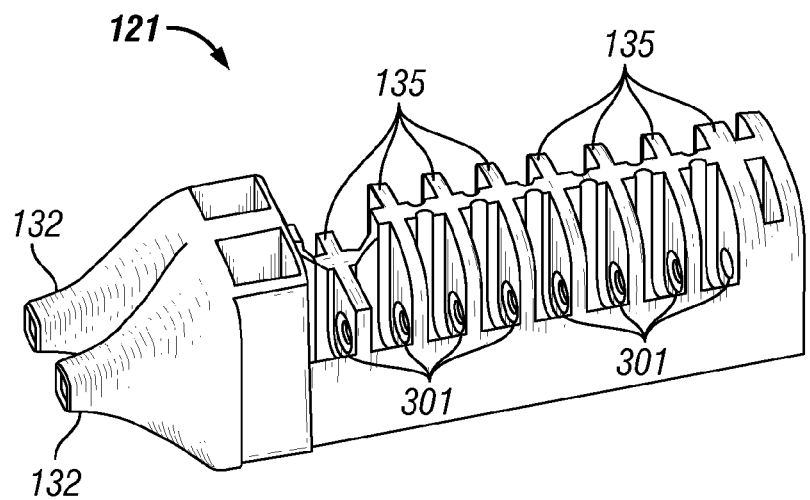
FIG. 3

HEADER DESIGN FOR IMPLANTABLE PULSE GENERATOR

CROSS-REFERENCE TO RELATED APPLICATIONS

This application is a continuation of U.S. application Ser. No. 12/100,814, filed Apr. 10, 2008, now U.S. Pat. No. 8,190,259, which claims the benefit of U.S. Provisional Application No. 60/910,941, filed Apr. 10, 2007, the disclosure of which is incorporated herein by reference.

TECHNICAL FIELD

The present application is generally related to a header design for an implantable pulse generator for accepting one or more stimulation leads.

BACKGROUND

Neurostimulation systems are devices that generate electrical pulses and deliver the pulses to nerve tissue to treat a variety of disorders. Spinal cord stimulation (SCS) is an example of neurostimulation in which electrical pulses are delivered to nerve tissue in the spine for the purpose of chronic pain control. Other examples include deep brain stimulation, cortical stimulation, cochlear nerve stimulation, peripheral nerve stimulation, vagal nerve stimulation, sacral nerve stimulation, etc. While a precise understanding of the interaction between the applied electrical energy and the nervous tissue is not fully appreciated, it is known that application of an electrical field to spinal nervous tissue can effectively mask certain types of pain transmitted from regions of the body associated with the stimulated nerve tissue. Specifically, applying electrical energy to the spinal cord associated with regions of the body afflicted with chronic pain can induce "paresthesia" (a subjective sensation of numbness or tingling) in the afflicted bodily regions. Thereby, paresthesia can effectively mask the transmission of non-acute pain sensations to the brain.

Neurostimulation systems generally include a pulse generator and one or more leads. The pulse generator is typically implemented using a metallic housing that encloses circuitry for generating the electrical pulses, control circuitry, communication circuitry, a rechargeable battery, etc. The pulse generation circuitry is coupled to one or more stimulation leads through electrical connections provided in a "header" of the pulse generator. Specifically, feedthrough wires typically exit the metallic housing and into a header structure of a moldable material. Within the header structure, the feedthrough wires are electrically coupled to annular electrical connectors. The header structure holds the annular connectors in a fixed arrangement that corresponds to the arrangement of terminals on a stimulation lead. When a stimulation lead is properly inserted within a port of the header, each terminal of the lead contacts one of the annular electrical connectors and, thereby, is electrically coupled to the pulse generating circuitry through the feedthrough wires.

A number of fabrication issues are associated with the selection of the material for the header. If a non-compliant high durometer material is selected for the header, additional complexity is typically provided to the header design to hold the electrical connectors in place. Also, the placement of the electrical connectors in such a header can be unduly difficult. Alternatively, if a compliant material is selected for the header, the header can be easily punctured or otherwise damaged by surgical tools during an implantation procedure.

SUMMARY

In one embodiment, an implantable pulse generator for electrically stimulating a patient comprises: a metallic housing enclosing pulse generating circuitry; a header mechanically coupled to the metallic housing, the header adapted to seal terminals of one or more stimulation leads within the header and to provide electrical connections for the terminals; the header comprising an inner compliant component for holding a plurality of electrical connectors, the plurality of electrical connectors electrically coupled to the pulse generating circuitry through feedthrough wires, wherein the plurality of electrical connectors are held in place in recesses within the compliant inner component, the header further comprising an outer shield component adapted to resist punctures, the outer shield component fitting over at least a portion of the inner compliant component.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

BRIEF DESCRIPTION OF THE DRAWINGS

FIGS. 2A and 2B depict known electrical connectors that can be utilized within a header according to representative embodiments.

FIG. 3 depicts a compliant inner component of a header according to one representative embodiment.

DETAILED DESCRIPTION

Some representative embodiments are directed to a header design for a neurostimulation system. The header design preferably comprises a compliant silicone component and a shield component of a non-compliant material. The silicone component and the shield component cooperate to provide seals between the lead electrodes and to provide a barrier to protect against damage or punctures from surgical tools used during implantation. The header design also preferably comprises an antenna component that defines a helical antenna path to support RF communications. Also, the antenna component is preferably adapted to facilitate coupling of the antenna with tissue of the patient to achieve a greater communication range for the implantable pulse generator.

Figure 1:
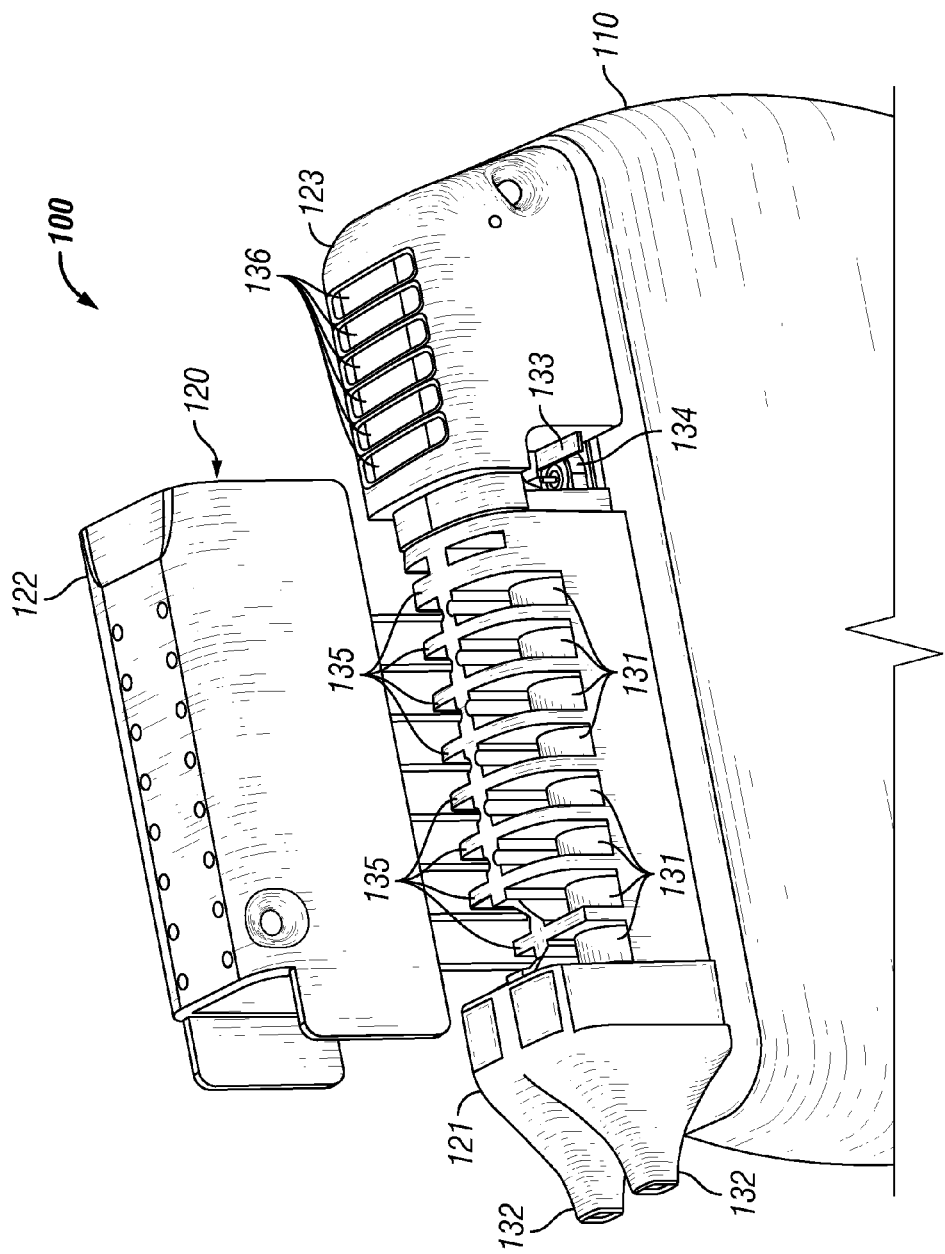
FIG. 1 depicts an implantable pulse generator that includes a header according to one representative embodiment.

FIG. 1 depicts implantable pulse generator 100 according to one representative embodiment. Implantable pulse generator 100 comprises metallic housing 110 that encloses the pulse generating circuitry, control circuitry, communication circuitry, battery, etc. of the device. An example of pulse generating circuitry is described in U.S. Patent Publication No. 20060170486 entitled "PULSE GENERATOR HAVING AN EFFICIENT FRACTIONAL VOLTAGE CONVERTER AND METHOD OF USE," which is incorporated herein by reference. A microprocessor and associated charge control circuitry for an implantable pulse generator is described in U.S. Patent Publication No. 20060259098, entitled "SYSTEMS AND METHODS FOR USE IN PULSE GENERATION," which is incorporated herein by reference. Circuitry for recharging a rechargeable battery of an implantable pulse generator using inductive coupling with an external charging device is described in U.S. patent Ser. No. 11/109,114, entitled "IMPLANTABLE DEVICE AND SYSTEM FOR WIRELESS COMMUNICATION," which is incorporated herein by reference. An example of a commercially available implantable pulse generator that may be adapted to include a header according to some representative embodiments is the EON® implantable pulse generator available from Advanced Neuromodulation Systems, Inc.

As shown in FIG. 1, header 120 comprises compliant inner component 121, non-compliant shield component 122, and antenna component 123. Compliant inner component 121 is preferably fabricated using an injection molding process and silicone based materials. Compliant inner component 121 is adapted to receive two stimulation leads (not shown) through strain relief elements 132, although header 120 could be alternatively adapted to couple to any suitable number of stimulation leads. To minimize the profile of implantable pulse generator 100, compliant inner component 121 is adapted to receive the stimulation leads in a side-by-side manner in one embodiment. Other embodiments may be configured to receive the stimulation leads in an above-below manner or even in an array-like manner for several stimulation leads.

Compliant inner component 121 is adapted to hold a plurality of electrical connectors 131 for each stimulation lead. Specifically, compliant inner component 121 comprises a plurality of recesses defined between respective wall structures 135 in which electrical connectors 131 are disposed. The compliant material characteristic of component 121 holds electrical connectors 131 in place by applying an elastomeric force. Electrical connectors 131 are spaced apart in relation to the spacing of the terminals of the stimulation leads intended to function with implantable pulse generator 100. Each electrical connector 131 is electrically coupled to pulse generation circuitry within metallic housing 110 through a respective feedthrough wire as is known in the art. Compliant inner component 121 is shown in isolation in FIG. 3. Apertures 301 within walls 135 are shown in FIG. 3 for the respective stimulation leads.

Typically, electrical connectors 131 are fabricated using an outer conductive annular or ring-like structure. Within the ring-like structure, one or more conductive members are held to engage a respective terminal of the stimulation lead. An example of known connector 200 is shown in FIG. 2A in which a canted spring is held within a conductive ring. Such connectors are commercially available from Bal Seal, Inc. of Foothill Ranch, Calif. Another example of known connector 250 is shown in FIG. 2B in which a conductive disk having arcuate connector tabs is held within a conductive ring as shown in U.S. Patent Publication No. 20050107859, entitled "SYSTEM AND METHOD OF ESTABLISHING AN ELECTRICAL CONNECTION BETWEEN AN IMPLANTED LEAD AND AN ELECTRICAL CONTACT," which is incorporated herein by reference. It shall be appreciated that other types of electrical connectors could be employed such as "block electrical connectors" which are known in the art. Also, different types of electrical connectors could be employed within the same header in any suitable configuration.

Figure 4:
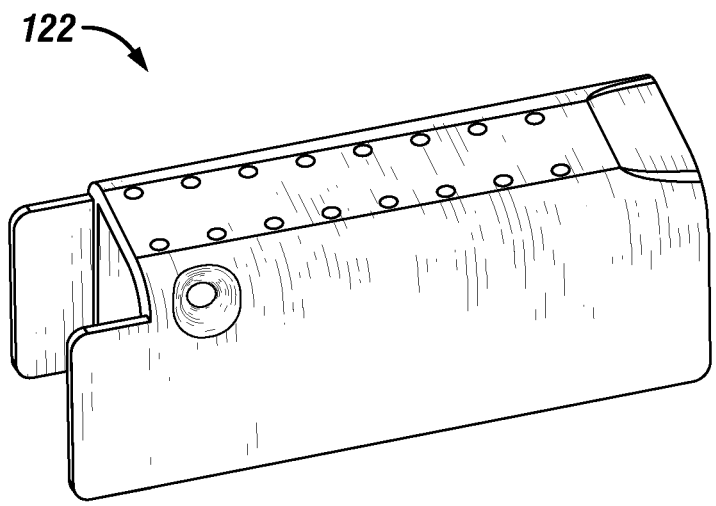
FIG. 4 depicts a shield component of a header according to one representative embodiment.

Shield component 122 (shown in isolation in FIG. 4) is adapted to fit over a significant portion of and mechanically couple to inner compliant component 121. Shield component 122 may also be adapted to fit over a portion or all of antenna component 123. When header 120 is fully assembled and stimulation leads are placed in header 120 through strain relief elements 132, the various conductive elements are sealed within the components of header 100. Specifically, when implantable pulse generator 100 is implanted within a patient, the electrical components are sealed and are prevented from contacting bodily fluids. Additionally, shield component 122 is fabricated from a relatively hard material to prevent damage to or puncture of compliant inner component 121. Specifically, if a sharp object used during the implantation procedure were to contact compliant inner component 121 directly, compliant inner component 121 could be punctured somewhat easily. The puncture could allow entry of body fluids and cause the patient to experience electrical stimulation in the subcutaneous implantation pocket. By utilizing a suitable material for shield component 122, compliant inner component 121 is protected from sharp surgical tools, needles, staples, and the like. An example of a suitable material for shield component 122 is a relatively high durometer Bionate® polycarbonate urethane.

Figure 5:
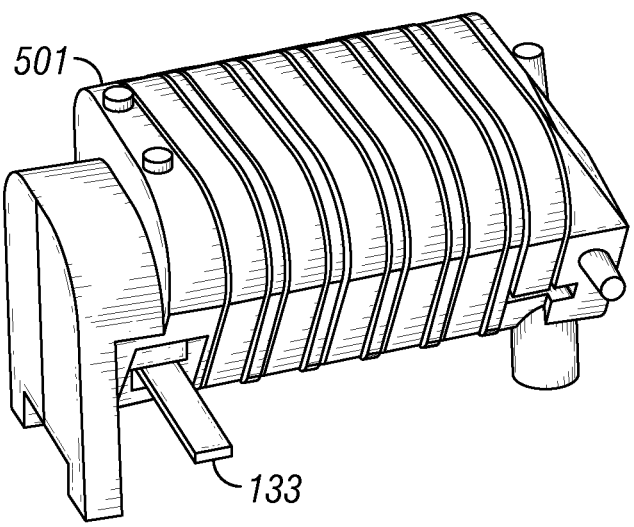
FIG. 5 depicts a structure for holding an antenna in a helical manner according to one representative embodiment.

Header 120 comprises antenna component 123 to facilitate RF communication between the implantable pulse generator 100 and an exterior controller device (not shown). The exterior shell of antenna component 123 is preferably a relative high durometer polymer. In one preferred embodiment, the exterior shell of antenna component 123 is a relatively high durometer Bionate® polycarbonate urethane. Platinum ribbon 133 forms the actual far field antenna and is preferably wrapped around a helical path defined within the interior of antenna component 123. Preferably, the antenna and communication circuitry enable wireless communications within a range of several meters. In one embodiment, platinum ribbon 133 is wrapped around molded polymer component 501 (shown in FIG. 5) which is enclosed within the exterior shell of antenna component 123. Polymer component 501 may provide any suitable number of revolutions for antenna ribbon 133.

Referring again to FIG. 1, platinum ribbon 133 is coupled to communication circuitry within metal housing 110 through feedthrough 134. The upper segments of platinum ribbon 133 are disposed immediately below slots 136 of exterior shell of antenna component 123. Slots 136 are formed by reducing the thickness of the polymer material of the exterior shell at the appropriate locations. The reduced thickness of the polymer material at these locations promotes the efficiency of the coupling of the RF signal with tissue of the patient. Such coupling facilitates a greater communication range for the RF signal.

Antenna 123 is preferably fully insulated from contact with human tissue by header 120 so that no corrosion products from the conductor of the antenna enter tissue, and, there is little surface impedance variation caused by fibrosis, scar tissue, etc, after implant. Surface impedance variation on the conductor may cause the distribution of radiating current density to change, possibly in a manner which deleteriously affects the radiation pattern outside the human body. Furthermore, gross surface impedance alterations may alter the amount of total electromagnetic energy radiated from/or into the antenna by causing intended emitted/absorbed energy to be reflected back to the transmitter.

The skewed cross-section shape of antenna 123 is preferably an inverted triangle with finite radius curves replacing triangle vertices. In one embodiment, the lowest, rounded, vertex is designed to be furthest from the straight top segment of each section, so that the enclosed area maximizes the storage of magnetic energy. But it is not so close to the conductive ("ground") surface of the enclosure that coupling to the enclosure is more than a small fraction of the coupling from the top segment to tissue. In that way, RF displacement current is provided with a lower impedance path from top segments of the antenna, much lower than that between lowest rounded vertices.

In some embodiments, the lowest rounded vertices may have any radius of curvature up to and including half the width of header 120. Or, as small as the minimum bend radius of conductor 133 according to some embodiments. However, as the radius of vertex curvature decreases, the RF electric field flux density increases in proximity to that vertex. The coupling to the enclosure would increase, and so to compensate those vertices would have to be displaced closer to the top segments of antenna 123. This would reduce the magnetic energy storage ("inductance") of each spiral revolution, or "turn" of the antenna. The intent of some embodiments is to optimize the inductance per turn with the ("electrostatic") coupling between turns so that the overall impedance of the antenna maximizes coupling into human tissue along the top sections of antenna 123, while also presenting an easily-matched impedance at the antenna feed terminal. The schematic 600 (FIG. 6) shows the approximate lumped element equivalent circuit.

The intent of some embodiments is to enhance emission from the top of the antenna, with a return path through human tissue, such that the current density distribution maximizes radiation outside the human body. The alignment of antenna 123 is preferably adapted such that directions of maximum radiation power density tend to be located symmetrically either side of the antenna mid-plane. The optimum electric field polarization direction is transverse to the antenna mid-plane. There would be a null (minimum) of the transverse polarization radiation intensity in the antenna mid-plane, provided the surrounding medium (human tissue) was isotropic and homogeneous.

Figure 6:
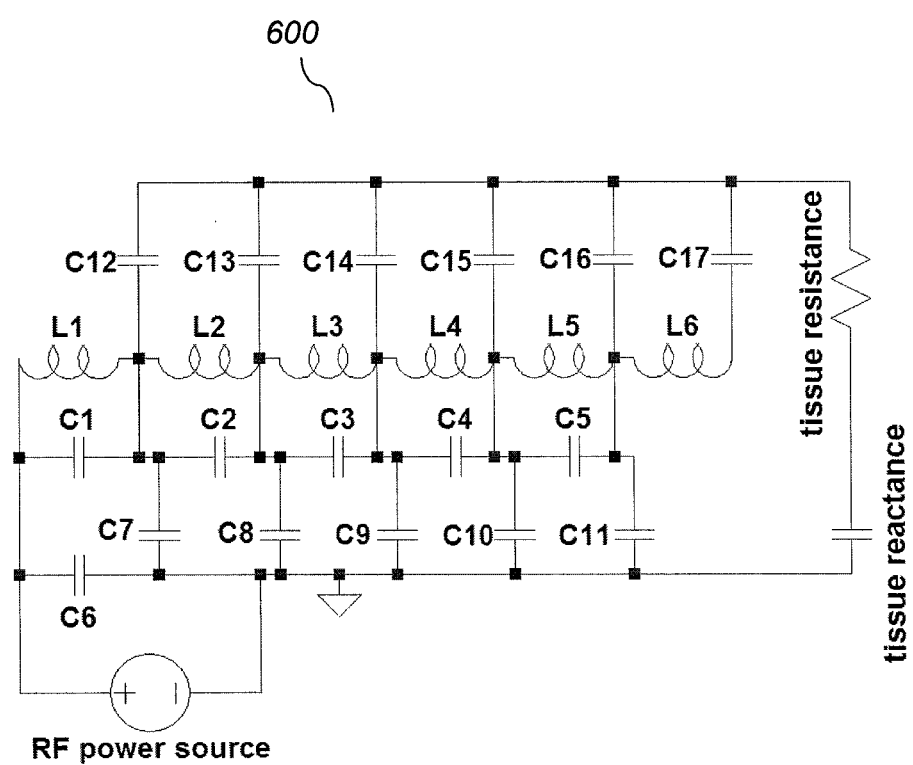
FIG. 6 depicts a schematic of an equivalent circuit for an antenna according to one representative embodiment.

Each complete path ("revolution") of inverted triangle with curved vertices, mentioned above, connects conductively with the adjacent triangular paths at one location, so that the complete antenna consists of multiple inverted triangular spiral elements connected together. The approximate equivalent circuit is shown in FIG. 6, for the example of a six turn inverted triangular spiral antenna (6T ITSA).

The conductor 133 of antenna 123 preferably consists of a metal strip presenting a large surface area along the top segments of the antenna, so that capacitances (C12-17, above) are maximized for a given thickness of insulation (dielectric), having a certain dielectric constant. For example, a rectangular cross section with a surface resistance per unit area much less than the surface reactances per unit area, presented by C12-17, at the radio frequency of operation.

Although certain representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate when reading the present application, other processes, machines, manufacture, compositions of matter, means, methods, or steps, presently existing or later to be developed that perform substantially the same function or achieve substantially the same result as the described embodiments may be utilized. Accordingly, the appended claims are intended to include within their scope such processes, machines, manufacture, compositions of matter, means, methods, or steps.

What is claimed is:

1. An implantable pulse generator for electrically stimulating a patient, comprising:
    a metallic housing enclosing pulse generating circuitry;
    a header mechanically coupled to the metallic housing, the header adapted to seal terminals of one or more stimulation leads within the header and to provide electrical connections for the terminals;
    the header comprising an inner compliant component for holding a plurality of electrical connectors and an outer component, wherein (i) the inner compliant component is an integral, single piece of compliant material, (ii) the inner compliant component comprises a plurality of walls defining a plurality of recesses, (iii) the electrical connectors are held in the plurality of recesses by an elastomeric force applied by the plurality of walls, (iv) the plurality of walls comprise a plurality of apertures defining two respective parallel channels through the inner compliant component, (v) the outer component is fit over at least a portion of the inner compliant component containing the plurality of electrical connectors to cover electrical connectors within the inner compliant component, and (vi) the electrical connectors are electrically coupled to the pulse generating circuitry through feedthrough wires.

2. The implantable pulse generator of claim 1 wherein the compliant inner component is fabricated using a silicone-based material.

3. The implantable pulse generator of claim 1 wherein the outer component is fabricated using a relatively high durometer polycarbonate urethane material.

4. The implantable pulse generator of claim 1 wherein the inner compliant component comprises one or more strain relief components for receiving one or more stimulation leads.

5. The implantable pulse generator of claim 1 wherein the header further comprises:
    an antenna component having an exterior shell enclosing an antenna for far field communications.

6. The implantable pulse generator of claim 5 wherein the exterior shell is adapted to couple RF power from the antenna to fluid or tissue of the patient when the implantable pulse generator is implanted within the patient.

7. The implantable pulse generator of claim 5 wherein the exterior shell of the antenna component is fabricated using a relatively high durometer polycarbonate urethane material.

8. The implantable pulse generator of claim 5 wherein the antenna component comprises an inner molded structure around which the antenna is wound.

9. The implantable pulse generator of claim 5 wherein the antenna is a helical antenna.

10. The implantable pulse generator of claim 5 wherein the outer shield component is placed over a portion of the antenna component where the antenna is electrically coupled to a feedthrough to communication circuitry within the metallic housing.

11. The implantable pulse generator of claim 5 wherein the exterior shell of the antenna component comprises a plurality of slots having reduced thickness in the exterior shell, wherein the antenna is immediately disposed beneath the slots of the exterior shell.

12. The implantable pulse generator of claim 1 wherein the header is adapted to receive two stimulation leads in a side-by-side manner.

* * * * *